US010244976B2

(12) United States Patent
Herrala et al.

(10) Patent No.: US 10,244,976 B2
(45) Date of Patent: Apr. 2, 2019

(54) DEVICE FOR MEASURING MUSCLE SIGNALS

(71) Applicant: Fibrux Oy, Vimpeli (FI)

(72) Inventors: Mika Herrala, Vimpeli (FI); Markku Vimpari, Oulu (FI); Pasi Tavi, Kuopio (FI); Juha Lampela, Oulu (FI)

(73) Assignee: FIBRUX OY, Vimpeli (FI)

( * ) Notice: Subject to any disclaimer, the term of this patent is extended or adjusted under 35 U.S.C. 154(b) by 0 days.

(21) Appl. No.: 15/738,920

(22) PCT Filed: Jun. 22, 2015

(86) PCT No.: PCT/FI2015/050452
§ 371 (c)(1),
(2) Date: Dec. 21, 2017

(87) PCT Pub. No.: WO2016/207471
PCT Pub. Date: Dec. 29, 2016

(65) Prior Publication Data
US 2018/0177447 A1 Jun. 28, 2018

(51) Int. Cl.
*A61B 5/00* (2006.01)
*A61B 5/22* (2006.01)
(Continued)

(52) U.S. Cl.
CPC ............ *A61B 5/222* (2013.01); *A61B 5/0004* (2013.01); *A61B 5/04014* (2013.01); *A61B 5/0488* (2013.01); *A61B 5/0492* (2013.01); *A61B 5/224* (2013.01); *A61B 5/4519* (2013.01); *A61B 5/7257* (2013.01); *A63B 22/0605* (2013.01);
(Continued)

(58) Field of Classification Search
CPC ....... A61B 5/0488; A61B 5/222; A61B 5/053; A63B 24/0062; A63B 24/0075; A63B 2024/0065
See application file for complete search history.

(56) References Cited

U.S. PATENT DOCUMENTS

| 5,361,775 A | 11/1994 | Remes et al. |
| 5,776,073 A | 7/1998 | Garfield et al. |

(Continued)

FOREIGN PATENT DOCUMENTS

WO 2012056114 A1 5/2012

OTHER PUBLICATIONS

Ki Young Lee: "Estimating muscle fatigue of the biceps brachii using high to low band ratio in EMG during sotonic exercise"; International Journal of Precision Engineering and Manufacturing, vol. 10, No. 3, pp. 147-153; Jul. 2009.
(Continued)

*Primary Examiner* — Max Hindenburg
(74) *Attorney, Agent, or Firm* — Ziegler IP Law Group, LLC

(57) ABSTRACT

A device or a system for measuring muscle signals. A system may include at least one processor, memory including computer program code, the memory and the computer program code configured to, with the at least one processor, cause the system to perform at least the following: measure a signal from a muscle to obtain a muscle activation signal; carry out at least one transform on the muscle activation signal to obtain a muscle activation spectrum; and determine a muscle state indicator from the muscle activation spectrum by using signal characteristics from a first and a second band of the muscle activation spectrum.

19 Claims, 8 Drawing Sheets

(51) Int. Cl.

| | |
|---|---|
| A63B 71/06 | (2006.01) |
| A63B 22/06 | (2006.01) |
| A61B 5/04 | (2006.01) |
| A61B 5/0492 | (2006.01) |
| A61B 5/0488 | (2006.01) |
| G16H 20/30 | (2018.01) |
| A63B 22/00 | (2006.01) |
| A63B 24/00 | (2006.01) |
| A61B 5/11 | (2006.01) |

(52) U.S. Cl.
CPC ......... *A63B 71/0622* (2013.01); *G16H 20/30* (2018.01); *A61B 5/0024* (2013.01); *A61B 5/1108* (2013.01); *A61B 5/6831* (2013.01); *A61B 5/6833* (2013.01); *A61B 5/726* (2013.01); *A61B 2503/10* (2013.01); *A61B 2505/09* (2013.01); *A61B 2560/0443* (2013.01); *A61B 2560/0462* (2013.01); *A63B 22/0056* (2013.01); *A63B 22/0076* (2013.01); *A63B 2024/0093* (2013.01); *A63B 2071/063* (2013.01); *A63B 2220/30* (2013.01); *A63B 2220/34* (2013.01); *A63B 2220/40* (2013.01); *A63B 2220/44* (2013.01); *A63B 2220/51* (2013.01); *A63B 2220/64* (2013.01); *A63B 2225/02* (2013.01); *A63B 2230/085* (2013.01); *A63B 2230/60* (2013.01)

(56) References Cited

U.S. PATENT DOCUMENTS

| | | | |
|---|---|---|---|
| 6,115,627 | A | 9/2000 | Street |
| 6,350,220 | B1 | 2/2002 | Milburn et al. |
| 2004/0181159 | A1 | 9/2004 | Kuo et al. |
| 2005/0283205 | A1 | 12/2005 | Lee et al. |
| 2010/0268104 | A1 | 10/2010 | Lee et al. |
| 2012/0184871 | A1 | 7/2012 | Jang et al. |

OTHER PUBLICATIONS

Search Report; dated May 23, 2018 by the European Patent Office; European Patent Application 15896234.0.

Allison et al. "The relationship between EMG median frequency and low frequency band amplitude changes at different levels of muscle capacity." Clinical Biomechanics 17 (2002), Received Jan. 18, 2002; accepted Apr. 23, 2002, Elsevier Science Ltd. PII:S0268-00033-5, 7 pages.

Soo et al. "Estimation of handgrip force using frequency-band technique during fatiguing muscle contraction." Journal of Electromyography and Kinesiology 20 (2010), Accepted Aug. 28, 2009, Elsevier Ltd, doi: 10.1016, 9 pages.

Yassierli et al."Utility of traditional and alternative EMG-based measures of fatigue during low-moderate level sometric efforts." Journal of Electromyography and Kinesiology 18 (2008), Accepted Aug. 7, 2006, Elsevier LTD, doi: 10.1016, 11 pages.

Soo et al., "The relationship between changes in amplitude and instantaneous mean frequency at low and high frequency bands during dynamic contraction." Abstract article of the 2nd International Conference on Bioinformatics and Biomedical Engineering. May 16, 2008, 5 pages.

Sparto et al. "Wavelet and Short-Time Fourier Transform Analysis of Electromyography for Detection of Back Muscle Fatigue." IEEE Transactions on Rehabilitation Engineering, vol. 9, No. 3, Sep. 2000, 5 pages.

Wang et al. "Fatigue Related Electromyographic Coherence Analysis between Agonistic Elbow Flexion Muscles" 2011 4th International Congress on Image and Signal Processing Oct. 15, 2011, doi:10.1109/CISP.2011.6100785, 5 pages.

Cifrek et al. "Surface EMG based muscle fatigue evaluation in biomechanics", Clinical Biomechanics 24 (2009), Accepted Jan. 28, 2009, Elsevier Ltd. doi: 10.1016/j.clinbiomech.2009.01.010, 15 pages.

International Preliminary Report on Patentability, Application No. PCT/FI2015/050452, dated Aug. 8, 2017, 19 pages.

Written Opinion of the International Searching Authority, Application No. PCT/FI2015/050452, dated Oct. 8, 2015, 7 pages.

International Search Report, Application No. PCT/FI2015/050452, dated Oct. 8, 2015, 5 pages.

DEVICE FOR MEASURING MUSCLE SIGNALS

BACKGROUND

Athletes often want to follow their performance in various ways. One way to follow the exercise is to measure muscle signals using electrodes. Surface electromyography (sEMG) is a technique for measuring electrical activity produced by skeletal muscles. EMG detects electrical potential generated by muscle cells, and the measured signal is called an electromyogram. However, there do not exist good ways to guide the training accurately enough.

There is, therefore, a need for a solution that provides an improved way to implement the measurements and analysis of muscle signals for the purpose of guiding exercise.

SUMMARY

Now there has been invented an improved method and technical equipment implementing the method, by which the above problems are alleviated. Various aspects of the disclosed embodiments include a system, an exercise system, and a computer readable medium comprising a computer program stored therein, and a method which are characterized by what is stated in the independent claims. Various embodiments of the present disclosure are disclosed in the dependent claims.

According to a first aspect, a system may comprise at least one processor, memory including computer program code, the memory and the computer program code configured to, with the at least one processor, cause the system to perform at least the following: measure a signal from a muscle to obtain a muscle activation signal, carry out at least one transform on said muscle activation signal to obtain a muscle activation spectrum; and determine a muscle state indicator from said muscle activation spectrum by using signal characteristics from a first and a second band of said muscle activation spectrum.

According to a second aspect, an exercise system may comprise at least one exercise device, at least one processor, memory including computer program code, the memory and the computer program code configured to, with the at least one processor, cause the system to perform at least the following: measure a signal from a muscle to obtain a muscle activation signal, carry out at least one transform on said muscle activation signal to obtain a muscle activation spectrum, determine a muscle state indicator from said muscle activation spectrum by using signal characteristics from a first and a second band of said muscle activation spectrum, and control said at least one exercise device based on said muscle state indicator.

Other aspects may comprise a method and a computer program product as described in the claims.

The user may perform a power span determination before an exercise to determine the first and the second bands from the muscle activation spectrum. Determination of a muscle state indicator may be carried out using signal characteristics from the bands. For example, the ratio of the mean powers over the bands may be calculated. The changes in the calculated ratio may be followed and the level of muscle fatigue may be estimated during exercise.

DESCRIPTION OF THE DRAWINGS

In the following, various embodiments of the present disclosure will be described in more detail with reference to the appended drawings, in which.

DESCRIPTION OF EXAMPLE EMBODIMENTS

In the following, several embodiments of the present disclosure will be described in the context of a method for determining a state of a muscle and indicating the state to a user. It is to be noted, however, that the invention is not limited to the example embodiments. In fact, the different embodiments have applications in any environment where measuring and/or analyzing muscle signals are required.

Figure 1A:
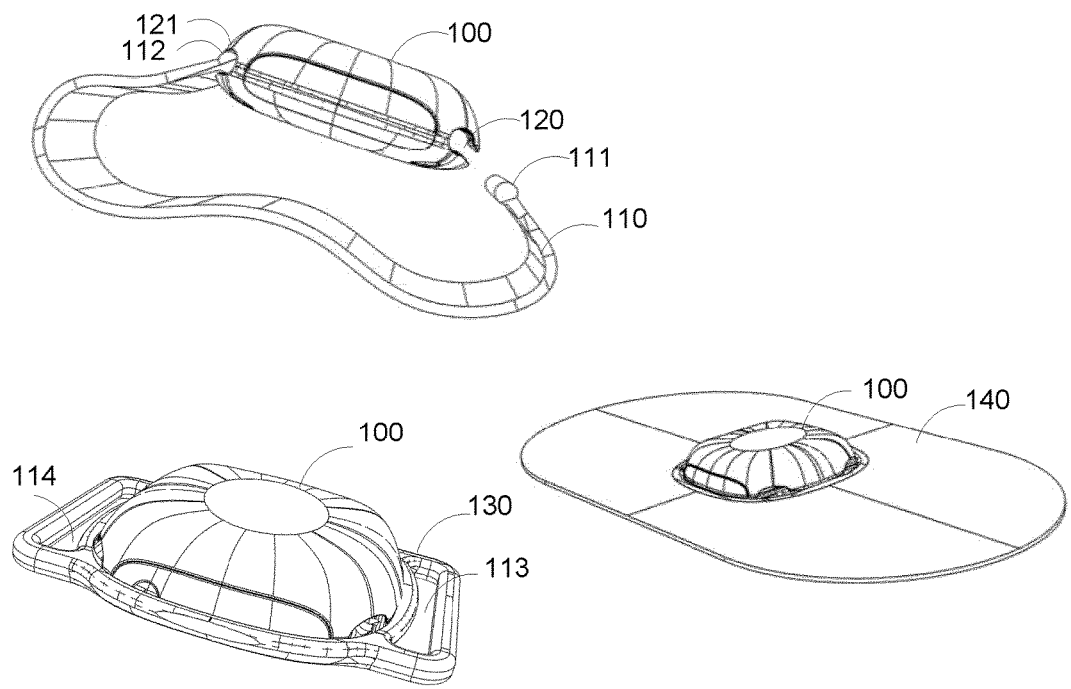
FIGS. 1a, 1b, 1c and 1d show example of a measurement unit and an attachment strap, and examples of electrode arrangements for measuring a muscle signal.

FIG. 1a shows an example of a measurement unit and an attachment strap. The measurement unit 100 may be attached to the strap 110 by clicking the ends 111,112 of the strap to grooves 120, 121. There may be alternative methods to wear the measurement unit. For example, there may be a holder/casing 130 with loops 113, 114 attached to the grooves 120, 121 of the measurement unit 100, through which the strap 110 or another kind of belt may be threaded. The advantage of this kind of attachment/detachment mechanism is that the user may have several straps and one measurement unit which can be easily moved from one strap to another. Different straps may be attached around different muscles. This way, dressing and undressing of the straps is not needed during the exercise to be able to measure signals from different muscles. Alternatively, the measurement unit 100 may be attached to a pad 140, which may be adhesive on the other side and may be attached on the skin. The casing 130 and the pad 140 may comprise an opening which enables the connection between the skin and the electrodes which may be integrated in the measurement unit 100.

Figures 1B, 1C, 1D:
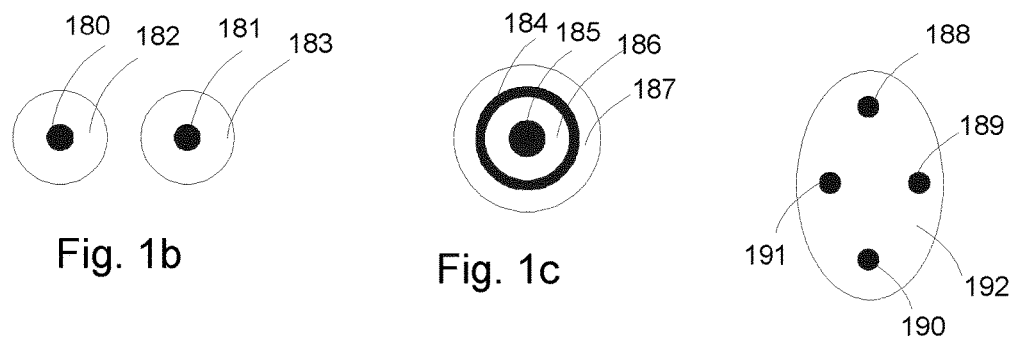

The measurement unit may contain electrodes. FIGS. 1b, 1c and 1d show examples of electrode arrangements for measuring a muscle signal. In FIG. 1b an electrode pair is shown. The electrodes 180 and 181 may be surrounded by electrical insulators 182 and 183 such as plastic, glass, porcelain, or air. In the case of air, the electrode may be essentially without any solid state insulator. The electrodes may be pieces of conducting material such as metal, semiconductor, carbon, conducting plastic or a composite material such as silver/silver-chloride mixture. The electrodes may be circular, rectangular, symmetric or asymmetric, or round or elongated in shape. The insulators 182, 183 may be common to both electrodes, i.e. be physically the same object or two objects connected to each other, or they may be separate. What has been said about the materials and setup of the electrodes in case of an electrode pair may apply mutatis mutandis to other setups illustrated in FIGS. 1c and 1d. The shape of the lead field of an electrode pair such as in FIG. 1b is such that the electrode pair essentially picks a signal from the muscle at the same depth as the distance between the electrodes 180 and 181. When the distance between the electrodes of the electrode pair is approximately 1 cm or less, very muscle specific data may be acquired. If electrodes pick up signals from a large volume, there may be crosstalk between muscles. With accurate recording, small changes in exercise posture may be detected.

The distance between the electrodes may vary depending on which muscle is concerned. Therefore, there may be different measurement units for different muscles. When an electrode setup comprises more than one electrode pair with differing distances between the electrodes of the pair (e.g. that of FIG. 1d), it may be possible to choose which electrode pair would be used in the measurements. If the user wants to measure signals of a large muscle, such as quadriceps, the distance between the electrodes in the measurement unit may be larger, e.g. 1-1.2 cm, than when the user wants to measure signals of smaller muscle, such as a biceps, when the distance between the electrodes may be e.g. 0.8-1 cm.

FIG. 1c shows a planar electrode setup. The electrodes 184 and 185 concentric and pick up essentially a so-called Laplacian signal, i.e. a derivative signal of the one picked up by an electrode pair. The Laplacian electrode may be sensitive to signal sources below the electrode. The electrodes 184 and 185 may be separated and/or surrounded by insulators 186 and 187.

FIG. 1d shows another planar electrode setup. There are four electrodes 188, 189, 190 and 191 making up two electrode pairs in a cross-form setting. The electrodes may be surrounded by an insulator 192. The electrodes 188 and 190 may be spaced apart by a different distance than the electrodes 189 and 191. It may be possible to choose which electrode pair would be used in the measurements.

There may be a ground element at least partially or completely surrounding the electrodes or electrode setups of FIGS. 1b, 1c and 1d. The ground element may not be an active member in the signal acquisition, and the ground element may be merely a conducting object without any active elements or without being connected to the acquisition electronics in any way. The ground element may work to restrict the lead field of the electrode arrangement so that it even more precisely picks up signals below the arrangement and is insensitive to signals coming from the side. In addition, the ground element may protect the electrodes from picking up ambient electromagnetic noise. The cover of the measurement unit may act as a ground element.

The measurement unit may be connected to a computer, or to a smartphone, tablet, watch, bike computer or other suitable device like controller of a cross trainer or ergometer at a gym, through a communication connection, such as Bluetooth. The placement of the measurement unit may be set in the application using a user-interface, wherein the user may set, by e.g. dragging and dropping, the measurement unit symbols on top of the image of a muscle in question of an illustrated body. In case the contact between the skin and the electrode is good enough, it may be indicated to the user in a way that the color of the measurement unit symbol changes to green, for example.

The user may wear two, or another number of, measurement units at the same time. The units may be labelled for example with a number, e.g. unit1 and unit2. The user may check which unit is on the leg and which unit is on the arm. This may be good to know and ensure when the user wants to follow the measurements of both measurement units at the same time during the exercise, and the measurements, e.g. signals or spectra of the signals, are labelled with number, e.g. spectrum1 and spectrum2, or muscle1 and muscle2, or biceps_left and biceps_right. The checking may be carried out by using accelerometer or haptic sensors, or some other sensors, integrated in the measurement unit. When the user shakes/touches the measurement unit1, the user may see in the application that the measurement unit symbol1 is for example blinking.

A system may be caused to measure a signal from a muscle to obtain a muscle activation signal. Then, at least one transform may be carried out on said muscle activation signal to obtain a muscle activation spectrum. A muscle state indicator may be determined from said muscle activation spectrum by using signal characteristics from a first and a second band of said muscle activation spectrum.

The signal characteristics may comprise power of the signal on the first and on the second band. A ratio may be formed between signal characteristics of the first band and the signal characteristics of said second band. For example, mean power over the band may be used in forming the ratio.

Figure 2:
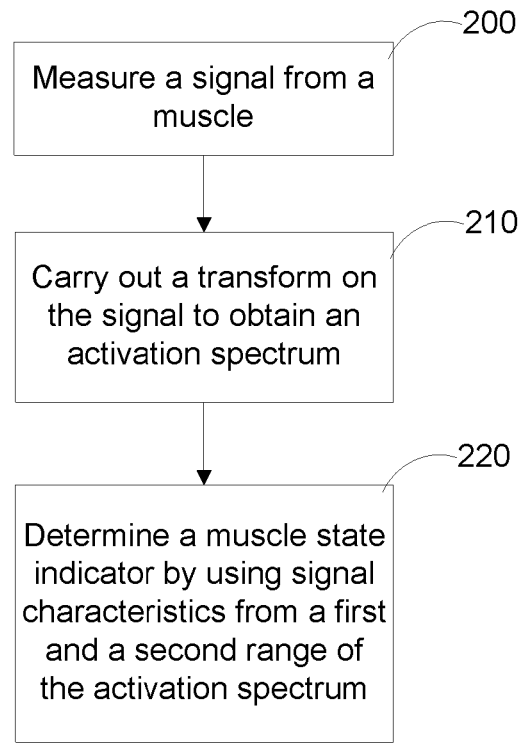
FIG. 2 shows a flowchart of a method for determining a state of a muscle.

FIG. 2 shows a flowchart of a method for determining a state of a muscle. At phase 200, a signal from a muscle at a first time instance may be measured to obtain a first muscle activation signal. The signal may be measured using an electrode arrangement, for example, which is capable of measuring the electrical activity in the muscle. The signal from a muscle, i.e. EMG signal, may be measured by placing the electrodes on the surface of the skin.

At phase 210 at least one transform on said muscle activation signal may be carried out to obtain a muscle activation spectrum. The transform from the time domain to frequency domain may be Fourier transform or Fast Fourier transform (FFT), for example. Transformation may also be carried out using another suitable transform, such as wavelet transform.

At phase 220 a muscle state indicator may be determined from the muscle activation spectrum. Determination may be carried out by using signal characteristics from a first and a second band of the muscle activation spectrum. The energy, or the power of the spectrum may be determined, for example, from the y-axis (amplitude) of the spectrum in FIG. 3a.

The bands may be determined from a spectrum that is measured during a maximum voluntary contraction. During maximum voluntary contraction the user tense or loads the muscle as hard as one can. The contraction may be held for couple of seconds, e.g. 3-10 seconds. Measured spectrum during the maximum voluntary contraction may be used to determine the bands. Maximum voluntary contraction test may be used to determine a maximum for both bands. During a minimum voluntary contraction test, the user may e.g. flex the arm very lightly. With this procedure called a power span determination, it may be possible to determine the maximum activation level of a muscle, and it may be carried out for different muscles separately. When the power span determination is carried out before an exercise, it may be possible to determine the characteristic spectrum for a fresh muscle which is not fatigued.

State of a muscle, for example fatigue, may be determined by using the ratio of mean powers over the two frequency bands. This flipping feature may provide an indication of fatigue regardless of the individual differences between people.

The first and the second band of said muscle activation spectrum may be partially non-overlapping in frequency or completely non-overlapping in frequency. Therefore, it may be possible to compare the powers of two bands at one time instance.

The first and the second band may be determined at different time instances and may be at least partially overlapping in frequency. Therefore, it may be possible to follow the power of one band as a function of time, i.e. the total activity of a muscle. In this case, the band may cover a wide frequency range, e.g. 10-250 Hz.

Figure 3A:
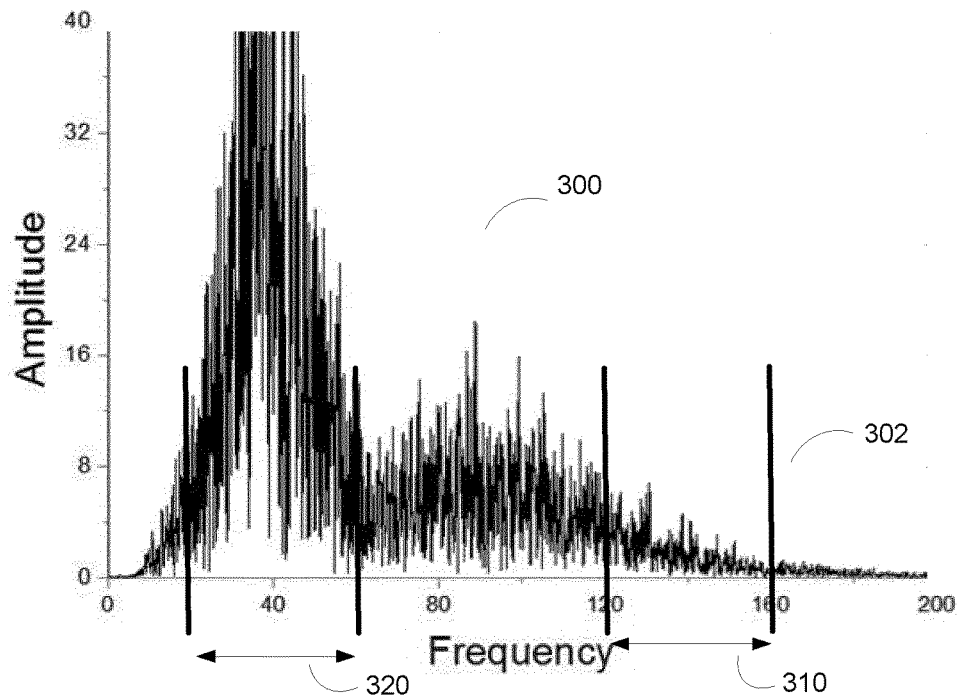
FIGS. 3a, 3b and 3c show examples of spectra of muscle signals and a muscle activity graph.

FIG. 3a shows an example of a signal measured during maximum voluntary contraction that has been transformed from time domain to frequency domain. The end of the spectrum 300 may be determined to be the point 302 wherein the amplitude of the spectrum falls to e.g. 3-10%, essentially 5%, of the maximum power. Then, a width of a first band 310 may be determined to cover e.g. 20-30%, essentially 25% of the width of the frequency spectrum at the upper end of the spectrum 300. A width of a second band 320 of the muscle activation spectrum 300 may be determined to cover 40 Hz around a maximum amplitude peak (not visible in the figure) of the spectrum 300, that is, 20 Hz on both sides of the peak. Alternative way to determine a band around the maximum peak is to use the full width at half maximum. There may also be other alternative ways. For example, the second band may be pre-set to cover a range of 20-60 Hz, or 30-70 Hz. The width of the first band may be pre-set to cover 20-30% of the width of the spectrum at the upper end of the spectrum.

For both bands 310, 320 it may be possible to determine a reference power value. The reference power value(s) may be used in determining the ratio of signal characteristics from the first and the second band of the muscle activation spectrum. For example, the reference power value may be the mean power value over the band. Alternatively, it may be the maximum power value or the minimum power value or the median power of the band on a sub-band of the band. The reference power value may be determined using a function, or it may be extrapolated/interpolated. The mean power value may be determined using the signals measured at a plurality of time points. For example, the user may carry out the maximum voluntary contraction or the minimum voluntary contraction test for three times. Then, the bands may be determined as described earlier, and the mean power may be calculated for each band. Then, the mean value of the mean powers may be calculated and determined to be the reference power value for the specific band. Alternatively, the user may carry out the maximum voluntary contraction or the minimum voluntary contraction by holding the contraction for longer time, e.g. 10-30 s. The bands may be determined at a plurality of time points, for example at 10 s, 20 s and 30 s, and the mean power may be calculated for each band. Then, the mean value of the mean powers may be calculated and determined to be the reference power value for the specific band.

If the determined reference power value changes during the exercise, it may be updated automatically. Essentially, if the mean power value over the band reaches a new maximum, i.e. a higher value than the value reached during the maximum voluntary contraction performed before the exercise, the reference power value may be updated. The updating of the reference power value during the exercise may be omitted if it is noticed that there are undesired artifacts in the spectrum. This may be evident due to unrealistic shape of the spectrum which may mean that there are too much low frequencies present in the spectrum, or there is distractive noise or AC grid hum (50 Hz or 60 Hz) present. For example, the noise is detected using known noise detection methods, and based on this detection, updating may be prevented. Hence, updated reference power values may be determined for said first reference power values during an exercise, wherein said updated reference power values are higher than said first reference power values. The updated reference power values may be used in determining said ratio of signal characteristics from said first and said second band of said muscle activation spectrum. When the reference power value is updated, i.e. a new maximum has been reached, it may be indicated to the user, e.g. with a text "New Max!".

There are different ways to carry out the power span determination. The power span determination may be carried out for each muscle separately. Another way to do the calibration (power span determination) is to use a scale factor which may be determined for different muscles, e.g. statistically. In this case, the user does the power span determination for one muscle and the power span for other muscles may be determined using the scale factor. The scale factor may be determined beforehand for each muscle of the specific user using the power span determination. Alternatively, there may be a list or a table or a chart saved in a computer or in a cloud where the scale factors may be listed according to age, gender, activity level, body mass index or some other characteristic. A scale factor may be automatically searched and picked from the list. If the user has calibrated an agonist-antagonist pair on the left side, the user may choose to use the same calibration on the right side, in which case the scale factor may be 1. It may be useful to do a separate calibration since there may be differences in the strengths of the muscles on different side of the body of the user.

Figure 3B:
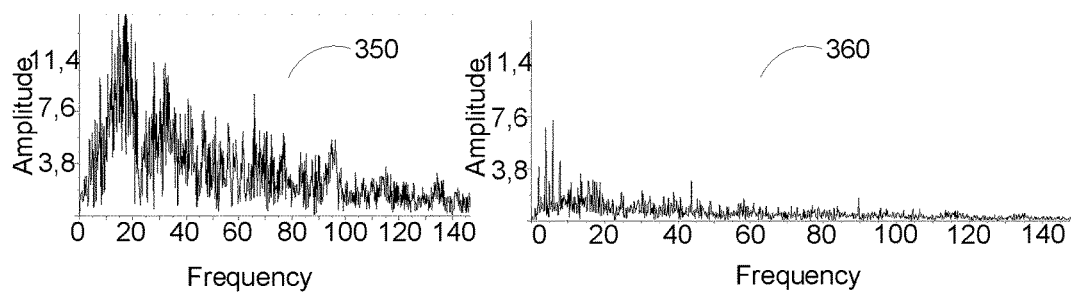

FIG. 3b shows examples of power spectra of muscle signals. The spectrum 350 is of a signal measured right after an exercise, i.e. when the rest has started and the spectrum 360 is of a signal measured at the end of the rest.

Figure 3C:
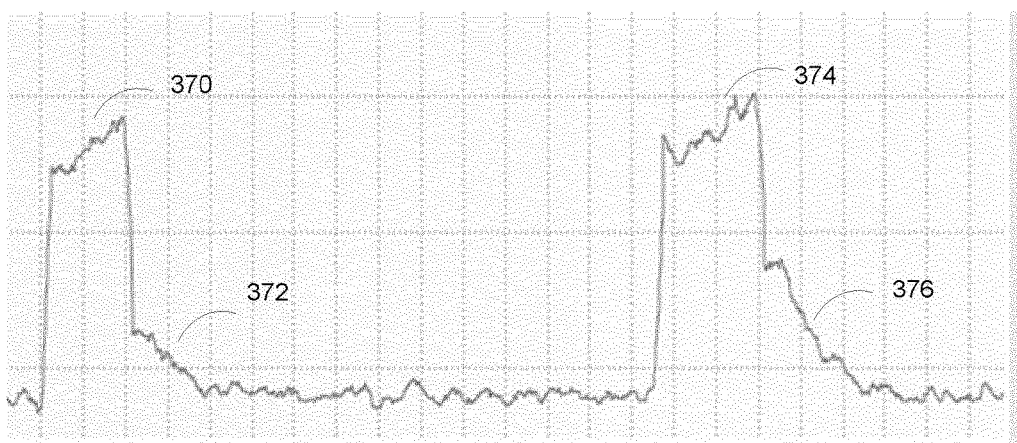

Recovery state of a muscle may be obtained by examining muscle signals at rest after the exercise. The decay or the decrease of the power of the signal after active exercise can be used to determine an estimate of recovery time. FIG. 3c shows the power signal according to time. The signal may be calculated by averaging the power over the frequency range at different time points. For example, the mean power may be calculated over the frequency range of 10-200 Hz or 10-250 Hz. For example, the mean power may be calculated with a time window of 250 ms (i.e. with the sampling frequency of 4 Hz) and one data point in the signal of FIG. 3c may represent a mean power over 2 s, i.e. 8 consecutive measurements. High power 370, 374 represents the signal measured during activity, which is followed by rest. After the activity, the level of the signal decreases. The form of the signal after the activity may be used to determine the recovery state of the muscle. The decay 372, 376 of the power of the signal may be exponential decay. The base may be 2, Euler's number, 10 or any suitable number. The decrease may be expressed by using an equation, for example a differential equation. A time constant may be determined for the decay, and the time constant may be used to estimate the recovery time. If the user performs a weight lifting exercise, the recovery time between the lifts may be determined. For example, if the determined time constant is 1 s, the user may be guided to recover 10*1 s before the next lift (or any other number of time constants). Alternatively, the recovery time between different exercises may be determined. For example, the user may be guided to wait 4 days before the next exercise comprising sprints.

Muscle fiber types can be divided into two main types: slow muscle fibers and fast muscle fibers. Fast fibers may be further categorized into subtypes. Each fiber type is unique in its ability to contract in a certain way. The slow muscles do not fatigue very fast, and therefore are great at helping athletes run marathons or bicycle for hours, for example. Fast fibers are much better at generating short bursts of strength or speed than slow muscles, but they fatigue more quickly. Fast fibers may be an asset to a sprinter since one needs to quickly generate a lot of force. Measurement of activation, fatigue and recovery levels of various types of muscles may be carried out by focusing on different frequency bands.

The user may follow different kinds of measurement results and/or receive exercise instructions during the exercise. The following may happen in various ways. For example, there may be a communication connection between the measurement unit and a computer or a smart phone. The user may follow the exercise on the user device screen, for example. The measured frequency spectrum may be shown to the user divided into bands with width of 10 Hz. The user may follow the power spectrum in real time on a screen, for example. The user may then see which types of muscle fibers (slow or fast or both) are activated and can optimize the exercise to match one's target. For example, when the user wants to improve speed, the user may follow the power spectrum or spectra and ensure that the fast muscles are recruited.

The target or the type of the exercise may be, for example, one of the following: strength, speed, endurance, hypertrophy. When the user starts the exercise, he can choose the type of the exercise using a computer application, for example. Determination of the type of exercise may also be made during the exercise based on the muscle activation spectrum. The type of the exercise may be used to determine, which kind of results may be shown to the user on the user device screen. For example, if the chosen or recognized exercise type is speed, the measurements of the fast muscles may be shown to the user. The type of the exercise may affect the signal processing parametrization, such as averaging time window.

The user may follow the power spectrum on the user device screen. It may be possible to set a user interface to show simultaneously the total power and the signal measured from fast and/or slow muscles. A target zone/training zone may be determined and shown to the user during the exercise. The displayed measurement result(s) may be determined based on the type of exercise.

If the user wants to improve speed, the user may be guided to focus the training on the fast muscles. The guiding may be done in various ways, for example by displaying a text on the screen, or by playing spoken instructions. During the exercise, the user may follow on the screen how the fast muscles are being recruited.

Occasionally, a shift of spectral energy to lower frequencies may be mistakenly interpreted as a fatigue of a muscle. In reality, this may only mean that the fast muscle fibers are not recruited. The wrong interpretation may be noticed by detecting the overall activity. If the overall activity, i.e. the mean power over the spectrum, is not close to the mean power of the spectrum measured during maximum voluntary contraction, it may be detected that the fatigue level may not be as high as indicated by the ratio of the signal characteristics of the first and the second bands. Then, the ratio of the signal characteristics may be corrected using a coefficient determined from the currently measured mean power over the spectrum and the mean power over the spectrum measured during maximum voluntary contraction.

The lead field depth equals the distance between the electrodes. In case the distance is large, for example 3-4 cm, the measurements are susceptible to signal filtering due to electrical properties of tissue. The signal detected from a muscle further away from the surface of the skin may be filtered due to electrical properties of the muscle tissue closer to the surface of the skin. When the muscle closer to the skin, i.e. the muscle being measured, is getting tired, the muscle further away from the surface of the skin may compensate this fatigue. Since the signal from the muscle further away is filtered due to tissue, it may produce mistakenly lot central frequencies to the spectrum. This way, it covers the fatigue of the measured muscle, since the falling of the central frequencies is not detected. Picking the signals originating deep from the surface of the skin may be avoided by measuring with a sensor or a measurement unit having electrodes located near to each other, when the signal will be picked only from the muscle under the sensor, not from a muscle further away.

Figure 4A:
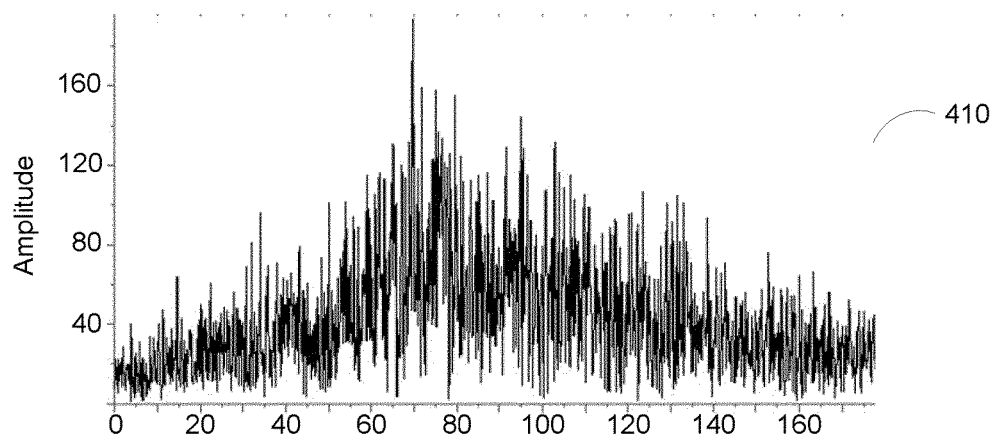
FIGS. 4a, 4b, 4c and 4d show examples of spectra of muscle signals measured from muscles at different states, and examples of estimated muscle fatigue and activity level.
Figure 4B:
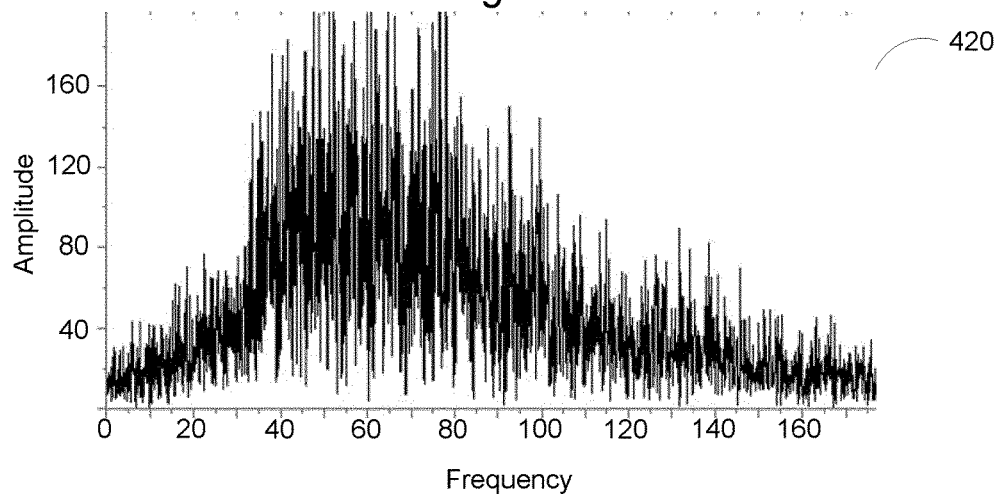
Figure 4C:
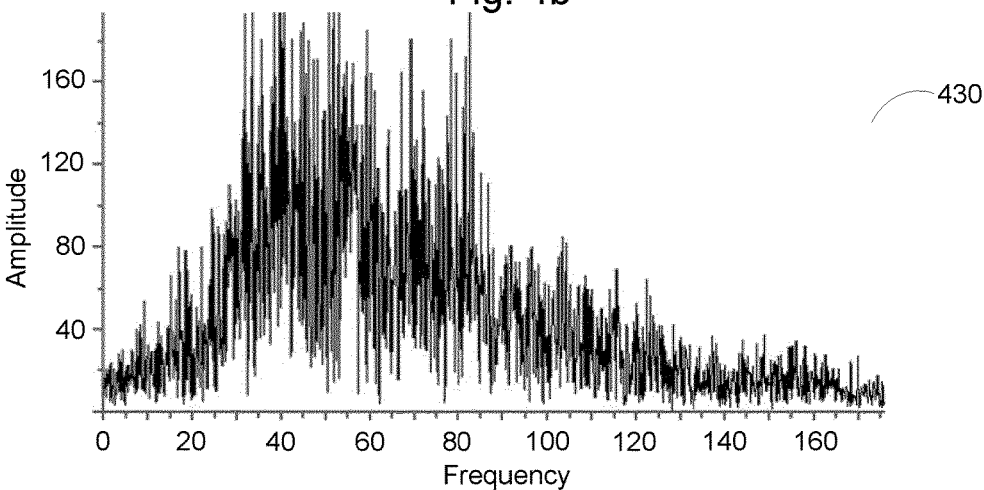

FIGS. 4a, 4b, 4c and 4d show examples of spectra of muscle signals measured from muscles at different states, and examples of estimated muscle fatigue and activity level. FIG. 4a shows a spectrum of a muscle signal measured from a fresh, non-fatigue, muscle. FIG. 4b shows a spectrum of a muscle signal measured from a muscle that is in a middle state, i.e. not fatigue but not fresh either. In the spectrum 420 of FIG. 4b it may be seen that the power of the central frequencies has increased and the power of the highest frequencies has decreased when compared to the spectrum 410 of FIG. 4a. FIG. 4c shows a spectrum of a muscle signal measured from a fatigue muscle. When the spectrum 430 of FIG. 4c is compared to the spectrum 420 of FIG. 4b, it may be seen that the power of lower frequencies has increased and the higher frequencies has decreased.

Figure 4D:
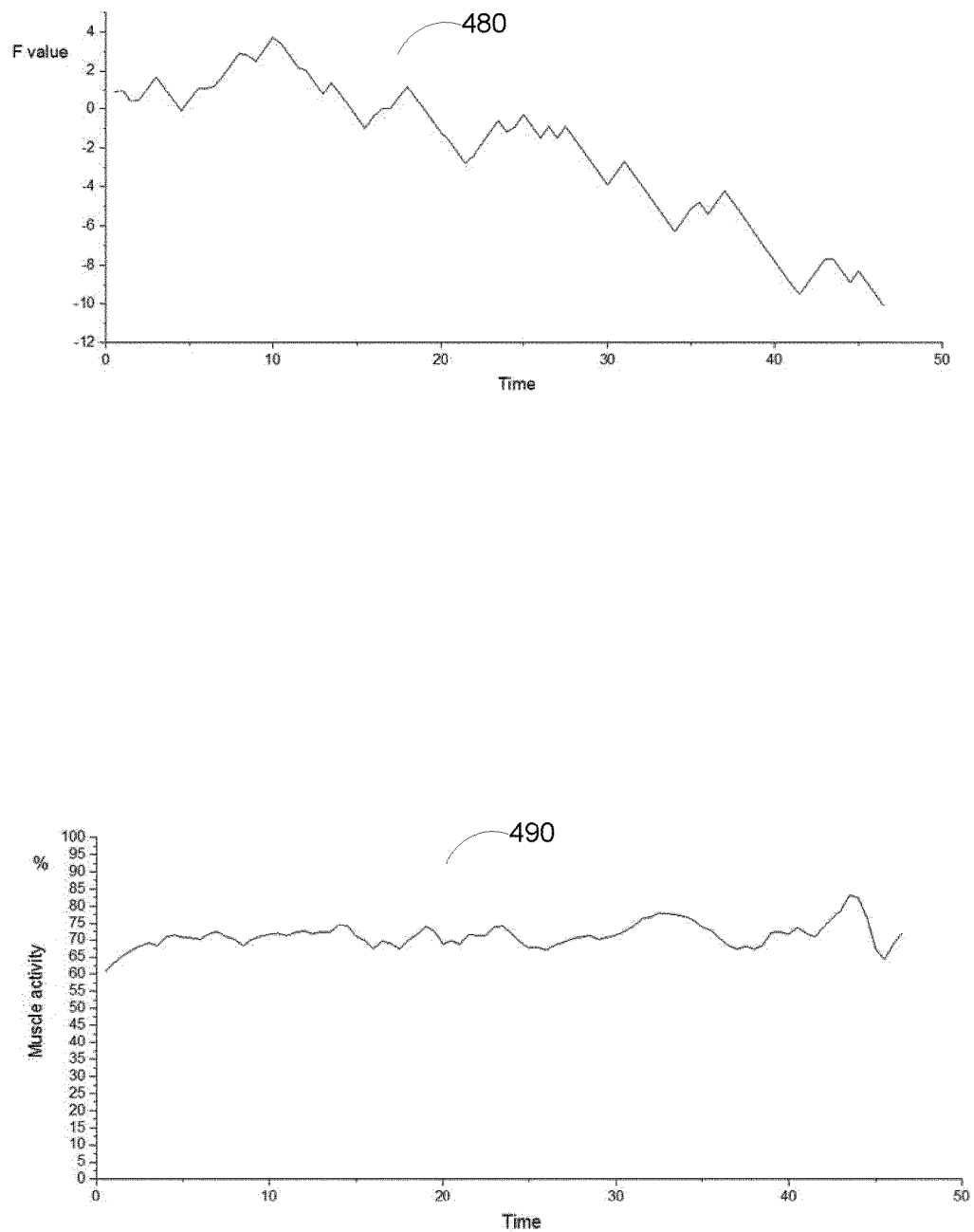

FIG. 4d shows example of an estimated fatigue level and a muscle activity level. Fatigue may be determined by using the ratio of mean powers over the two frequency bands which frequency bands may be determined by power span determination described earlier. The mean powers over the frequency bands determined during the exercise may be normalized with the reference power values determined during the maximum voluntary contraction, or by updating procedure during the exercise. The ratio of the mean powers, i.e. the F-value, may be set to be equal to 1 or 100% which describes the state of a fresh muscle at the beginning of the exercise. The graph 480 in FIG. 4d shows how the F-value behaves during the exercise. The scale may be normalized in a way that is shows the values between 0 and 1 or 0 and 100%, or some other range.

Let us go through an example of determining an F-value. The two frequency bands may be determined before an exercise during maximum voluntary contraction: first and second frequency band may be labelled as "high" and "low", respectively. The reference power values determined for these two bands may be $P_{max,high}$ and $P_{max,low}$. The signal characteristics determined during the exercise for both bands may be $P_{mean,high}$ and $P_{mean,low}$. Then, a ratio of signal characteristics may be computed as follows:

$$F = \frac{\frac{P_{mean,high}}{P_{max,high}}}{\frac{P_{mean,low}}{P_{max,low}}} = \frac{P_{mean,high}}{P_{mean,low}} \cdot \frac{P_{max,low}}{P_{max,high}}$$

The graph 490 describes the estimated muscle activity level during the exercise. It may be seen that the user has performed the exercise using approximately 70% of the maximum capacity of the muscles of the user. The mean power may be calculated over the frequency range of e.g. 10-250 Hz with a time window of approximately 250 ms (i.e. with the sampling frequency of 4 Hz) and one data point in the graph 490 may represent a mean power over approximately 2 s, i.e. 8 consecutive measurements. A personal range for the activity may be determined using the maximum and the minimum voluntary contraction tests. The measured power during the exercise may be compared to the personal maximum power to calculate the percentual activity. A trapezoidal equation may be used in determination of the individual activity range.

A threshold value or values may be determined for guiding the exercise. For example, the frequency band representing the fast muscle fibers may be analyzed and when the mean power over the band is under a predetermined threshold value, the user may be made aware of that using an audio signal, for example. Alternatively, the user may be alerted if a predetermined threshold value is not reached. Alternatives for the audio signal may be a light signal or some kind of a vibration, or haptics on the smart phone or on the measurement unit. The user may be warned also when the mean power is exceeding a predetermined threshold value.

A personal trainer may plan an exercise program for an aged person. A training zone may be determined comprising the fast muscles. The training zone may be determined based on the power span determination. The aged person may perform an exercise, e.g. using an exercise bicycle. If the resulting measurements are not included in the training zone, the user may be alerted.

A type of exercise may be received as an input, wherein said type of exercise is one or more of strength, speed or endurance, determining at least one threshold value for guiding said exercise and guiding said type of exercise using said muscle activation spectrum and said at least one threshold value. Alternatively, the type of exercise may be determined based on said muscle activation spectrum.

The guidance may also be done in a way that the classification of the exercise is told or indicated to the user after exercise or during exercise. For example, the user may be given an indication that the exercise mostly trained fast muscle cells, i.e. the exercise mostly improved speed. The indication may be a text on screen, for example "Good job! You improved speed!".

Figure 5:
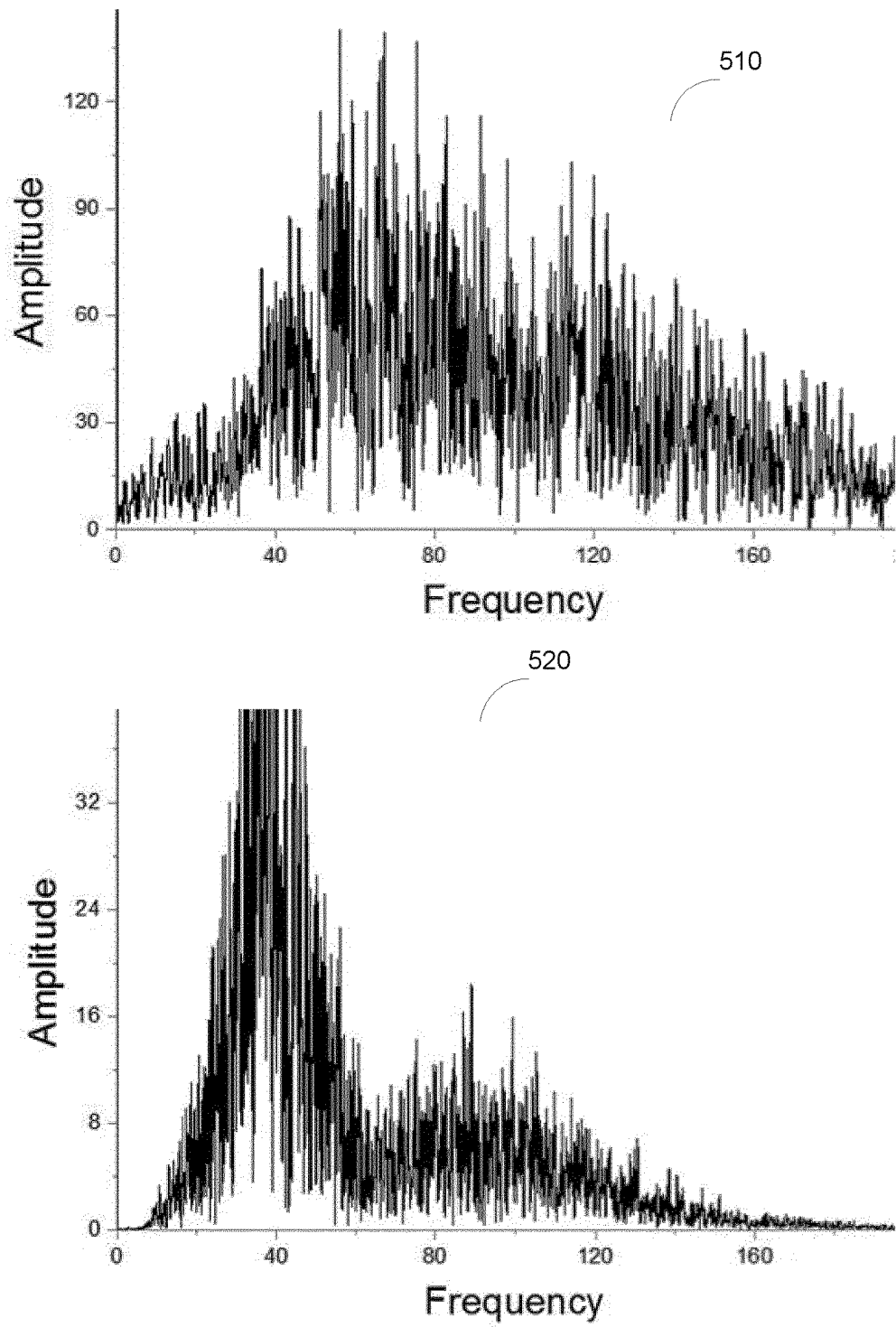
FIG. 5 shows examples of spectra of muscle signals measured from exercised and non-exercised muscles.

FIG. 5 shows exemplary maximum voluntary contraction signals of an exercised 510 and non-exercised 520 muscle. The frequencies of the spectrum of the exercised muscle 510 are more evenly distributed, and the central frequencies are prominent. The lower frequencies are prominent in the spectrum of the non-exercises muscle 520, and the high frequencies are almost absent. Maximum voluntary contraction test may be used to measure asymmetry between right and left sides of the user. For example, the user may do the maximum voluntary contraction test for both sides and if there is asymmetry, the user is guided to perform specific exercises to achieve better balance between different sides. The measured spectrum during maximum voluntary contraction test should show similar spectra for having a good balance.

If a right side muscle shows a spectrum resembling 510 and a left side muscle shows a spectrum resembling 520, there may be asymmetry between the right and left sides. Then, the user may be guided to focus on the training of the left side muscle. The guidance may be an audio signal saying "It seems that your left side muscle needs improvement".

Maximum voluntary contraction may be used as a muscle condition indicator showing the development potential for a muscle and for steering towards the right exercise type. The absence of high frequencies in the spectrum may indicate that the muscle is non-exercised, and there may be possibilities to achieve better strength for that muscle. If the shape of the spectrum is flat and the power values relatively low, the user may be guided to exercise maximum strength and speed. Measured activation, fatigue and recovery history information may be saved in an exercise diary and used for muscle development monitoring. The diary may be shared to other users, for example in social media or other service. The measurements and/or the saved exercises may be remotely monitored by a coach or a physiotherapist.

Figure 6:
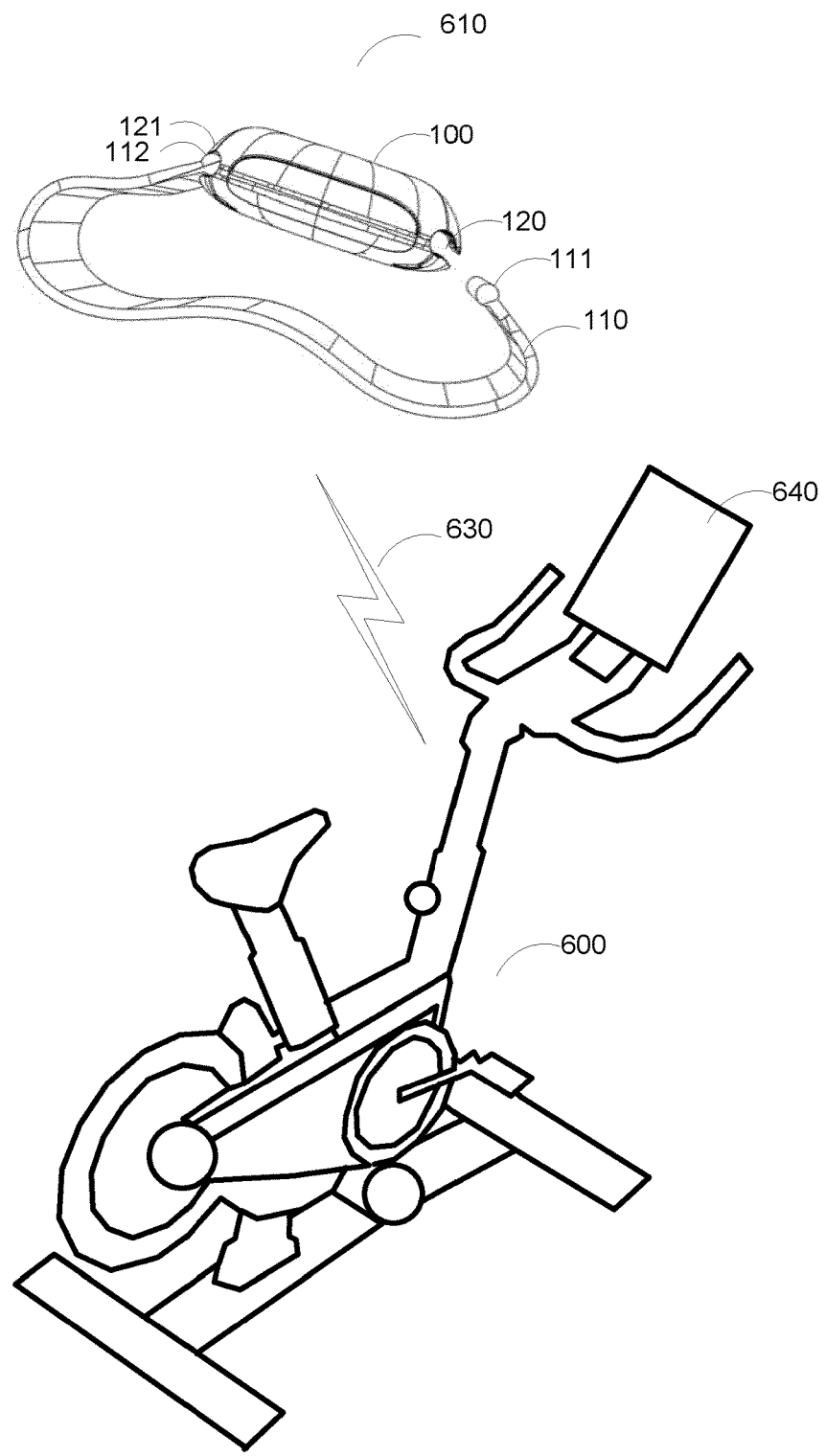
FIG. 6 shows an example of an exercise system.

FIG. 6 shows an example of an exercise device which may be controlled using the information received from the measurement unit. The measured muscle signal or the determined muscle state or other information received from the measurement unit 610 may be used to control the load produced by an exercise device, such as an exercise bicycle 600, or to control the speed or the slope angle of a treadmill, or to control the load produced by an ergometer. An ergometer may mean for example a stepper, indoor rower or a crosstrainer. There may be a communication connection 630 between the exercise bicycle 600 and the measurement unit 610 through which the information may be sent and received. Alternatively, or in addition, there may a communication connection between the exercise bicycle and a smart phone or a computer comprising the custom made training application. For example, the user may want to improve strength. Then, the user chooses that option from the settings of the measurement unit. The chosen exercise type, i.e. strength in this example, is sent from the measurement unit 610 to the control unit 640 of the exercise bicycle 600 through the communication connection 630. Then, the resistance or load of the bicycle may be automatically adjusted to be higher. Alternatively, the user may be guided to select from different built-in load profiles using the user interface of the exercise bicycle.

An example of a course of an exercise may be the following. The user enters a gym and attach the measurement unit to a target muscle on which one wants to focus on during training. This time the user wants to train the thighs. The user has a measurement unit for both thighs. Using an application run by a smart phone the user may drag and drop the measurement unit symbols to the corresponding muscles. Then, the user carries out the power span determination for another thigh, as described earlier. The user wants to use the same power span determination for both, right and left thighs, and therefore uses a scale factor of 1 when determining the power span for another thigh. Then, the mean power value is determined for both bands during maximum voluntary contraction. The ratio of these mean power values describes the state of a fresh muscle. The user chooses from the user settings that during training one wants to follow the percentile level of muscle performance in relation to the performance of the fresh muscle. Then, using an application run by a smart phone the user chooses a type of an exercise, which is endurance in this example. A communication connection is established between the measurement unit and the exercise bicycle, or between the smart phone and the exercise bicycle. The user starts training and starts measuring the muscle signals by turning on the measurement mode using the application. After some time of cycling, the user is alerted using a text on the smart phone screen that in order to improve endurance, the muscle activity level is too high, i.e. the muscle may get too tired too fast. Therefore, the resistance of the exercise bicycle is decreased by the user or automatically decreased based on a control signal from the measurement unit.

The various embodiments of the present disclosure can be implemented with the help of computer program code that resides in a memory and causes the relevant apparatuses to carry out the disclosed embodiments. For example, a device may comprise circuitry and electronics for handling, receiving and transmitting data, computer program code in a memory, and a processor or micro controller that, when running the computer program code, causes the device to carry out the features of the various embodiments.

It is obvious that the present disclosure is not limited solely to the above-presented embodiments, but it can be modified within the scope of the appended claims.

The invention claimed is:

1. A system for guiding a user in an exercise, the system comprising at least one processor, memory including computer program code, and at least one sensor configured to detect a signal from a muscle of the user, the memory and the computer program code configured to, with the at least one processor, cause the system to perform at least the following:

measure the signal from the muscle provided by the sensor to obtain a muscle activation signal during at least one contraction of said muscle;

convert said muscle activation signal from the time domain to the frequency domain to obtain a muscle activation spectrum;

determine a first band and a second band from the muscle activation spectrum measured during a maximum voluntary contraction of the muscle;

determine first reference power values for said first band and said second band from the muscle activation spectrum that is measured during the maximum voluntary contraction;

use said first reference power values in determining a ratio of signal characteristics from said first band and said second band of said muscle activation spectrum;

determine a muscle state indicator from said muscle activation spectrum by using said ratio of signal characteristics from the first band and the second band of said muscle activation spectrum; and guide the exercise using the determined muscle state indicator.

2. The system according to claim 1, wherein said signal characteristics comprise a power of said signal on said first band and on said second band, wherein the memory and the computer program code are further configured to cause the system to perform at least the following:

form a ratio between said signal characteristics of said first band and said signal characteristics of said second band.

3. The system according to claim 1, wherein the first band and the second band of said muscle activation spectrum are partially non-overlapping in frequency or completely non-overlapping in frequency.

4. The system according to claim 1, wherein the first band and the second band are determined at different time instances and are at least partially overlapping in frequency.

5. The system according to claim 1, wherein a width of said first band of said muscle activation spectrum is approximately 25% of an upper end of said muscle activation spectrum, wherein the upper end of said muscle activation spectrum is a point wherein power of said muscle activation spectrum falls to approximately 5% of maximum power.

6. The system according to claim 1, wherein a width of said second band of said muscle activation spectrum is approximately 40 Hz around a maximum power peak of said muscle activation spectrum.

7. The system according to claim 1, wherein said first band and said second band of said muscle activation spectrum are determined using a scale factor and the bands of a muscle activation spectrum of another muscle.

8. The system according to claim 1, the memory and the computer program code further configured to cause the system to perform at least the following:

determine first reference power values for said first band and said second band during the maximum voluntary contraction;

determine updated reference power values for said first reference power values during the exercise, wherein said updated reference power values are higher than said first reference power values; and use said updated reference power values in determining the ratio of signal characteristics from said first band and said second band of said muscle activation spectrum.

9. The system according to claim 1, the memory and the computer program code further configured to cause the system to perform at least the following:

determine a time constant from a decay of a measured muscle signal power level; and compute an estimate of recovery time based on said time constant.

10. The system according to claim 1, the memory and the computer program code further configured to cause the system to perform at least the following:

receive a type of exercise as an input, wherein said type of exercise is one or more of strength, speed or endurance;

determine at least one threshold value for guiding said exercise; and guide said type of exercise using said muscle activation spectrum and said at least one threshold value.

11. The system according to claim 1, the memory and the computer program code further configured to cause the system to perform at least the following:

determine a type of exercise based on said muscle activation spectrum;

determine at least one threshold value for guiding said exercise; and guide said type of exercise using said muscle activation spectrum and said at least one threshold value.

12. The system according to claim 10, the memory and the computer program code further configured to cause the system to perform at least the following:

determine at least one measurement result according to said type of exercise; and display said at least one measurement result to the user.

13. The system according to claim 11, the computer program code further configured to cause the system to perform at least the following:

determine at least one measurement result according to said type of exercise; and display said at least one measurement result to the user.

14. The system according to claim 1, further comprising at least one exercise device and the memory and the computer program code further causes the system to perform at least the following:

control said at least one exercise device based on said muscle state indicator.

15. The system according to claim 14, the memory and the computer program code further configured to cause the system to perform at least the following:

control resistance of said at least one exercise device based on said muscle state indicator.

16. The system according to claim 14, the memory and the computer program code further configured to cause the system to perform at least the following:
   guiding the user of said at least one exercise device to control resistance of said at least one exercise device based on said muscle state indicator.

17. The system according to claim 15, the memory and the computer program code further causes the system to perform at least the following:
   guiding the user of said at least one exercise device to control resistance of said at least one exercise device based on said muscle state indicator.

18. A computer program product embodied on a non-transitory computer readable medium, comprising computer program code configured to, when executed on at least one processor, cause an apparatus or a system to:
   measure a signal from a muscle to obtain a muscle activation signal during at least one contraction of said muscle;
   convert said muscle activation signal from the time domain to the frequency domain to obtain a muscle activation spectrum;
   determine a first band and a second band from the muscle activation spectrum measured during a maximum voluntary contraction of the muscle;
   determine first reference power values for said first band and said second band from the muscle activation spectrum that is measured during the maximum voluntary contraction;
   use said first reference power values in determining a ratio of signal characteristics from said first band and said second band of said muscle activation spectrum;
   determine a muscle state indicator from said muscle activation spectrum by using said ratio of signal characteristics from the first band and the second band of said muscle activation spectrum; and
   guide the exercise using the determined muscle state indicator.

19. A method for determining a state of a muscle of a user and guiding the user in an exercise based on the determined state, the method comprising using a device that includes at least one processor, a memory including computer program code, and at least one sensor configured to detect a signal from the muscle, wherein execution of the computer program code by the processor is configured to cause the device to:
   measure the signal from the muscle detected by the sensor using the processor to obtain a muscle activation signal during at least one contraction of said muscle;
   convert said muscle activation signal from the time domain to the frequency domain to obtain a muscle activation spectrum;
   determine a first band and a second band from the muscle activation spectrum measured during a maximum voluntary contraction of the muscle;
   determine first reference power values for a first band and a second band from the muscle activation spectrum that is measured during a maximum voluntary contraction of the muscle;
   use said first reference power values in determining a ratio of signal characteristics from said first band and said second band of said muscle activation spectrum;
   determine a muscle state indicator from said muscle activation spectrum by using said ratio of signal characteristics from the first band and the second band of said muscle activation spectrum; and
   guide the exercise based on the determined muscle state indicator.

* * * * *